US009488635B2

(12) United States Patent
Li et al.

(10) Patent No.: US 9,488,635 B2
(45) Date of Patent: Nov. 8, 2016

(54) PORE STRUCTURE ANALYZER BASED ON NON-CONTACT IMPEDANCE MEASUREMENT FOR CEMENT-BASED MATERIALS

(75) Inventors: Zongjin Li, Hong Kong (CN);
Shengwen Tang, Hong Kong (CN);
Youyuan Lu, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 784 days.

(21) Appl. No.: 13/333,124

(22) Filed: Dec. 21, 2011

(65) Prior Publication Data

US 2012/0158333 A1  Jun. 21, 2012

Related U.S. Application Data

(60) Provisional application No. 61/457,070, filed on Dec. 21, 2010.

(51) Int. Cl.
*G01N 33/38* (2006.01)
*G01N 27/02* (2006.01)
*G01N 27/04* (2006.01)

(52) U.S. Cl.
CPC .......... *G01N 33/383* (2013.01); *G01N 27/021* (2013.01); *G01N 27/048* (2013.01)

(58) Field of Classification Search
CPC .... G01N 33/383; G01N 33/38; G01N 27/08; G01N 27/02–27/24; G01N 27/60

USPC ........................................... 702/65
See application file for complete search history.

(56) References Cited

U.S. PATENT DOCUMENTS

| | | | | |
|---|---|---|---|---|
| 6,423,243 | B2 * | 7/2002 | Inoue | 252/62.62 |
| 6,556,001 | B1 * | 4/2003 | Wiegand et al. | 324/76.21 |
| 6,639,401 | B2 * | 10/2003 | Li et al. | 324/239 |
| 2009/0322557 | A1 * | 12/2009 | Robb et al. | 340/870.3 |
| 2011/0068807 | A1 * | 3/2011 | Kesil | G01N 27/023 324/633 |

OTHER PUBLICATIONS

Omran, Hesham; Sharaf, Khaled; Ibrahim, Magdy; "An All-Digital Direct Synthesizer Fully Implemented on FPGA," 2009; IEEE.*
Li, Zongjin; Xiao, Lianzhen; "Early-age hydration of fresh concrete monitored by non-contact electrical resistivity measurement;" Sep. 19, 2007; Cement and Concrete Research 38; p. 312-319.*
Bajorek, C; Krongelb, S; Romankiw, L; "A Permalloy Current Sensor;" Nov. 6, 1976; IEEE Transcations on Magnetics, vol. MAF-12, No. 6.*

(Continued)

*Primary Examiner* — Gregory J Toatley
*Assistant Examiner* — Terence Stifter, Jr.
(74) *Attorney, Agent, or Firm* — Nath, Goldberg & Meyer; Jerald L. Meyer; Stanley N. Protigal

(57) ABSTRACT

Measurement of the impedance and complex resistivity of a sample is used for measuring parameters resulting from a change in physical or chemical state. A variable frequency signal is provided by a transformer primary coil. A secondary coil of the transformer with a closed loop and electrically coupled said sample is monitored along with a leakage current sensor. Sampling at multiple signal frequencies is performed at the multiple signal frequencies.

21 Claims, 6 Drawing Sheets

(56) References Cited

OTHER PUBLICATIONS

Cabeza, M; Keddam, M; Novoa, X.R.; Sanchez, I; Takenouti, H; "Impedance spectroscopy to characterize the pore structure during the hardening process of Portland cement paste;" Aug. 25, 2005; Electrochimica Acta 51; p. 1831-1841.*

Excerpt from HP Impedance Analyzer Model 4191A; Section III.*

Wilson, J.G.; Whittington, H.W.; "Variations in the electrical properties of concrete with change in frequency;" Sep. 5, 1990; IEE Proceedings, vol. 137.*

Barsoukov, Evgenij; Macdonald, J. Ross; Impedance Spectroscopy Theory, Experiment, and Applications; 2005; John Wiley & Sons, Inc.; Second Edition, p. 1-26.*

Christensen, Bruce J.; Impedance Spectroscopy of Hydrating Cement-Based Materials: Measurement, Interpretation, and Application; Jul. 27, 1994; Journal of American Ceramic Society; vol. 77, No. 11.*

McCarter, W J; The Application of Impedance Spectroscopy to Cementitious Systems; May 1999; Solatron Limited; Technical Report No. 29.*

Torrents Josep M.; Pallas-Areny Ramon; Measurement of Cement Setting by Impedance Monitoring, 1997; IEEE Instrumentation and Measurement.*

Bandara T.M.W.J.; Mellander B.-E.; Evaluation of Mobility, Diffusion Coefficient and Density of Charge Carriers in Ionic Liquids and Novel Electrolytes Based on a New Model for Dielectric Response; Feb. 28, 2011; InTech.*

Zeynep Dilli; Intrinsic and Extrinsic Semiconductors, Fermi-Dirac Distribution Function, the Fermi Level and Carrier Concentrations; Mar. 2009; Enee 313.*

Wei, X.S., 'Interpretation of hydration process of cement-based materials using resistivity measurement', PhD Thesis, The Hong Kong University of Science and Technology, Hong Kong (2004).

Xiao, L.Z., 'Interpretation of hydration process of concrete based on electrical resistivity measurement', PhD Thesis, The Hong Kong University of Science and Technology, Hong Kong (2007).

Zhang, J., 'Microstructure study of cementitious materials using resistivity measurement', PhD Thesis, The Hong Kong University of Science and Technology, Hong Kong (2008).

McCarter, W.J. and Brousseau, R., 'The A.C response of hardened cement paste', Cem. Concr. Res. 20 (6) (1990) 891-900.

Gu, P., Xie, P., Fu, Y. and Beaudoin, J.J., 'A.C impedance phenomena in hydrating cement system: Frequency dispersion angle and pore size distribution', Cem. Concr. Res. 24 (1) (1994) 86-89.

Christensen, B.J., Coverdale, T., Olson, R.A., Ford, S.J., Garboczi, E.J., Jennings, H.M. and Mason, T.O., 'Impedance spectroscopy of hydrating cement-based materials: measurement, interpretation, and application', J. Am. Ceram. Soc. 77 (11) (1994) 2789-2804.

Mandelbort, B.B., 'The Fractal Geometry of Nature', (W. H. Freeman, San Francisco, 1982).

Yu, B.M., 'Analysis of flow in fractal porous media', Appl. Mech. Rev. 61 (5) (2008) 050801-1-050801-19.

Yu, B.M., 'Fractal analysis of permeabilities for porous media', AIChE. J. 50 (1) (2004) 46-57.

Liu, S.H., 'Fractal model for the ac response of a rough interface', Phys. Rev. Lett. 55 (5) (1985) 529-532.

Song, H.K., Jung, Y.H., Lee, K.H and Dao, L.H., 'Electrochemical impedance spectroscopy of porous electrodes: the effect of pore size distribution', Electrochim. Acta. 44 (20) (1999) 3513-3519.

Sapoval, B., Chazalviel, J.N. and Peyriere, J., 'Electrical response of fractal and porous interfaces', Phys. Rev. A. 38 (11) (1988) 5867-5887.

He et al (He Z and Li ZJ, Non-contact resistivity measurement for charaterisation of the hydration process of cement-paste with excess alkali, Advances in Cement Research, vol. 16, 2004).

Li, et al., Structural Renovation in Concrete, Taylor & Francis Mar. 12, 2009, ISBN-13:978-0415423717 ISBN-10:0415423716.

Li, et al., "Preliminary Interpretation of Portland Cement Hydration Process Using Resistivity Measurements" ACI Materials Journal, No. 100-M30, pp. 253-257, May-Jun. 2003.

* cited by examiner

PORE STRUCTURE ANALYZER BASED ON NON-CONTACT IMPEDANCE MEASUREMENT FOR CEMENT-BASED MATERIALS

BACKGROUND

Field

The present disclosure relates to measuring non-contact impedance (complex resistivity) measurement adopting the transformer principle. In particular, the disclosure relates to impedance and complex resistivity measurements in concrete and other materials transformed to a solid phase from a liquid phase.

Background

A hardened hydraulic cement-based material, such as Portland cement, is produced by the hydration reaction which is a complex chemical, physical and mechanical process that starts as soon as water is mixed with cement particles and turns the water-cement mixes into a stone-like material. This complex process is referred as to the hydration of cementitious materials. The main characteristic of the hydration is the reduction of porosity accompanied by the formation of the hydration products. The continuously evolving network of pores determines the ultimate physical and mechanical properties of the cementitious materials, including strength, permeability and durability. Considerable attention has been focused on the pore structure characterization. Experimental methods to measure pore structure characteristics of such cements include water adsorption, mercury intrusion porosimetry (MIP), helium pycnometry, solvent replacement, nuclear magnetic resonance relaxation (NMR), scanning electronic microscope (SEM), transmission electronic microscope (TEM), X-ray diffraction (XRD), and small angle X-Ray scattering. Among the several techniques that allow investigating the evolution of the microstructure of cement-based materials, those based on monitoring the electrical properties during the cement hydration process have received attention.

SUMMARY

Impedance of a sample resulting from a change in a physical or chemical state is measured, using signals provided by a signal generator with a frequency synthesizer. A transformer has a primary coil connected to the signal generator, and at least one of the primary and secondary coils is electrically coupled the sample. Multiple signal frequencies are sampled by causing sensing of signals from the signal generator as transmitted through the secondary coil of the transformer at the multiple signal frequencies and sensing of the leakage current.

The sampling can be performed by using a sympathetic impedance circuit having at least one of a primary reactive circuit and a secondary reactive circuit electrically coupled to the sample, and sampling the voltage across the secondary reactive circuit and leakage current as a function of the frequency-variable signal at multiple signal frequencies provided to the sympathetic impedance circuit.

BRIEF DESCRIPTION OF THE DRAWINGS

FIG. 3A shows the modulus of complex resistivity.

FIG. 3B shows the real part of complex resistivity.

FIG. 3C shows the imaginary part of complex resistivity.

FIG. 3D shows the phase lag of complex resistivity.

FIG. 3E is a diagram showing a modulus and differential modulus of complex resistivity.

FIGS. 4 A-C are graphic depictions which demonstrate the complex resistivity of the Cement Paste Example 2.

DETAILED DESCRIPTION

Overview

Figure 1:
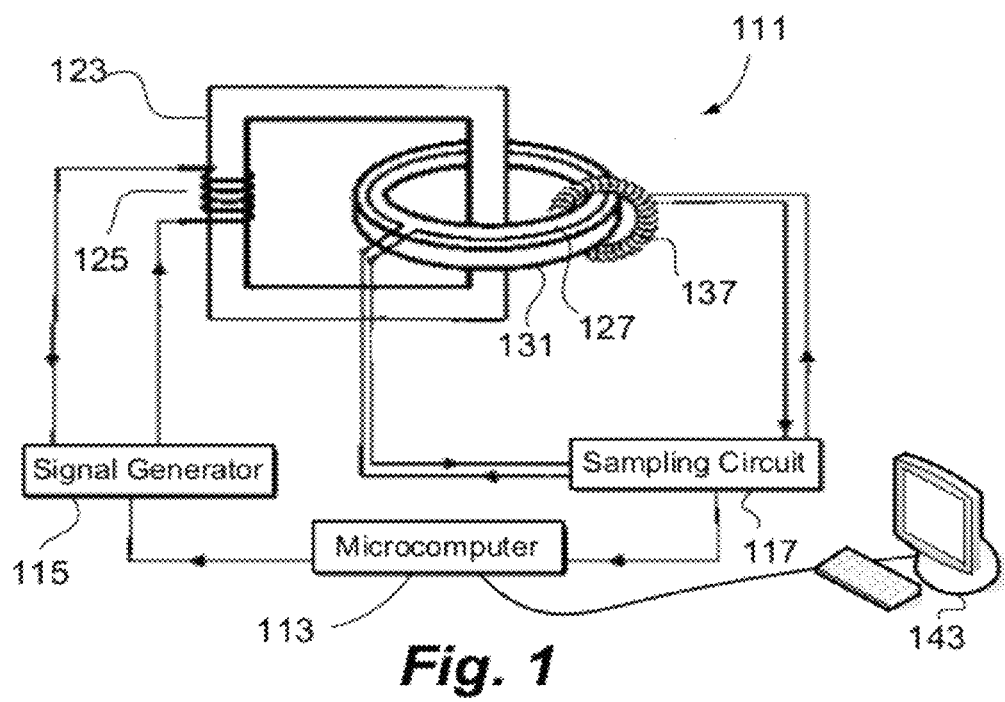
FIG. 1 is a schematic diagram of non-contact impedance (complex resistivity) measurement for a first example configuration.

Electrical methods have advantages over other methods in terms of sensitivity and fast processing. Electrical conduction through the hydrating cement-based system at the early cure age is almost entirely electrolytic. In addition, the electrical parameters, including the real part and imaginary part of impedance (complex resistivity), reflect the permeability, mobility, concentration and distribution of the charge carriers. Electrical measurements are sensitive to the complex factors affecting the microstructure of cement-based media, such as different water/cement ratios (w/c ratios), the different chemical compositions of cement and its hydration products and the use of particular minerals and other chemicals in the cement mixture. The phenomena that accompany the sol-gel transition, which occurs when water-cement mixes turn into an infinitely connected body, can also be evaluated using electrical methods. Useful information relative to microstructural changes, such as porosity and pore connectivity in hydrating cementitious materials, can also be determined from electrical methods. The impedance or complex resistivity of cement-based media is thus very informative and can be regarded as the fingerprints of cement hydration and its microstructure. Such studies lead to a more profound understanding of the evolution of the microstructure of the cement-based system. Electrical methods also have the advantages of being noninvasive and nondestructive and can be used to test the microstructure in situ.

Different electrical approaches exhibit different electrochemical mechanisms. Previous research on the electrical properties of cement-based materials can be roughly divided into two areas. In the first area, two electrodes are used and connected to a cement-based specimen for direct impedance measurements. Since any direct application of current to a cement or concrete specimen cannot avoid a polarization effect, these methods cannot obtain accurate results for the electrical resistivity of cement and concrete, although these methods have the advantage of being able to utilize a very wide frequency range of electrical stimulus.

In the second area, the concept of non-contact resistivity is proposed. A non-contact measurement device utilizes the inductive components to replace the electrodes. Thus, the problem involved in contact between electrodes and fresh cement paste, such as electrochemical reactions and shrinkage gap problems, can be eliminated in the system. This system has high accuracy, good reproducibility, and is useful for the study of microstructure evolution during the hydration process.

In one configuration, the inductive components include a transformer and current sensor, which replace electrodes. Alternately, other impedance devices may be used, such as capacitive sensors. It is found that the resistivity or impedance development curves from this kind of apparatus are similar to the curves of heat evolution of cement.

Five hydration stages could be identified by characteristic points on the differential resistivity curves, which are:
- dissolution stage;
- competition stage;
- acceleration stage;
- deceleration stage; and
- diffusion-controlled stage.

The hydration stages can be identified by characteristic points on differential resistivity curves.

The non-contact measurement can also determine the setting time of fresh concrete. Furthermore, the effect of type of cement, water/cement ratio (w/c ratio), curing time, chemical and mineral admixtures, and environmental change on hydration of cement-based materials have been investigated using this method. During investigation, it was found that there is a limitation in this system that a fixed frequency (1 kHz) alternating current (AC) is applied for measuring electrical resistivity of the specimen, which mainly reflects the porosity of specimen, and therefore cannot directly demonstrate the pore structure development in real time.

The disclosed techniques optimize non-contact measurements of concrete impedance resulting from applying a fixed frequency (1 kHz) alternating current (AC) to measure electrical resistivity of the specimen. The fixed frequency measurement mainly reflects the porosity of the specimen, and therefore cannot directly demonstrate the pore structure development in real time. To achieve an accurate measurement of resistivity for cement-based materials, the disclosed system (non-contact impedance measurement), which combines advantages of two areas mentioned above, applies different electrical parameters to impedance measurement. This system not only continues to implement the transformer principle but also changes the frequency domain of the electrical signal.

The disclosed techniques take advantage of an R-L-C (resistor-inductor-capacitor) model of the material under test. This is particularly useful in the case of hydrating cements, because the hydration process significantly affects the electrical conductivity of the material.

The non-contact impedance measurement also adopts the transformer principle. This system can apply different frequencies and different amplitudes of electrical stimulus onto materials and utilize an inductive component instead of metallic electrodes. In this system, the input sine wave signal is alternating voltage with amplitude modulation and can sweep the frequency range from about 1 kHz~100 kHz. The sine wave is applied onto the transformer via a high power amplifier. The secondary coil in the transformer is the cement paste which is cast into the ring-mold. The voltage and current in the cement-based material are measured by a current sensor and voltage detector, respectively. The data is transmitted to an external personal computer. All the data (voltage; current; the phase lag between them; temperature in the internal mold) are saved in a personal computer and are employed to analyze the impedance and complex resistivity of cement-based materials in real time. There are also no electrodes in this set-up; hence the interface problems between the electrodes and matrix are similarly eliminated. Furthermore, the calibration showed that 1 mol KCl electrical resistivity using this set-up was 0.091904 Ω·m at 20° C. The standard electrical resistivity quoted in engineering handbooks for 1 mol KCl is 0.09797 Ω·m at 20° C. The relative errors of the modulus and phase lag of complex resistivity are 6.19% and 4.4°, which demonstrate that this apparatus has a high precision.

The real part, imaginary part and phase lag of impedance and complex resistivity can be measured and used to interpret the hydration progress, maturity, strength development and porosity in cement-based materials, such as hydraulic cement based materials. In addition, the system can also be used for the electrochemical and dielectric measurement of liquid phase materials (molten glass, molten metal, toxic solution and biological solution), which have a very strong corroding effect on metallic electrodes. The liquid phase materials may be a liquid phase of a hydrating material such as hydrating cement. Alternatively, the liquid phase materials may be molten glass, molten metal, toxic solution, biological solution or other cement-based materials. The impedance data is useful in analyzing the mechanism of chemical reaction in such systems.

In the described examples, a transformer is given as an example of a sympathetic impedance device, in which electrical energy applied to a primary reactive circuit evokes a response in a secondary reactive circuit. While a transformer is described by way of example, the techniques described herein can be applied to other types of sympathetic impedance devices using reactive circuits. Such sympathetic impedance devices can include capacitors or active circuits, provided that the sample can be coupled to a secondary reactive device and respond to an electrical signal applied to the secondary or sympathetic reactive device.

Configuration

FIG. 1 is a schematic of a non-contact impedance (complex resistivity) measurement apparatus having a first example configuration. Shown are transformer 111, microcomputer 113, signal generator 115 and sampling circuit 117. Transformer 111 includes transformer core 123, primary coil 125 and secondary coil 127. Secondary coil 127 is mounted to or cast inside specimen ring 131, with specimen ring 131 provided as a sample. Leakage current sensor 137 surrounds a portion of secondary coil 127, but is physically separated from secondary coil 127.

In this example configuration, a single arm transformer core 123 is provided, and primary coil 125 is wound round the core 123 of transformer. In this system, secondary coil 127 makes a part of specimen ring 131 by mounting secondary coil 127 to specimen ring 131 or casting secondary coil 127 in specimen ring 131. Specimen ring 131 can be annular or rectangular according to which is easier to mold. Secondary coil 127 is constructed as a single coil surround on an upper surface of the specimen 131, and is able to measure the toroidal voltage of specimen ring 131.

Microcomputer 113 uses microcontrollers with integrated peripherals designed for real-time control applications. Microcomputer 113 has a math-optimized core to give designers the means to improve system efficiency, reliability, and flexibility. The amplitude and frequency of the signal can be altered by programming the microcomputer. The user can modify the parameters in the system to determine the required frequency domain, frequency step, frequency point, applied amplitude of the sine wave scanning timing per frequency and sampling interval, respectively. The impedance data of specimen 131 is sent to an external computer 143 by an appropriate data connection.

Signal generator 115 includes a Direct Digital Synthesizer (DDS) and a push-pull high power amplifier with amplitude compensation.

Transformer core 123 is constructed of manganese zinc ferrite with high amplitude permeability and low power loss.

Specimen 131 is cast in a mold, and combined with secondary coil 127, functions as part of secondary coil 127 in a closed loop. The toroidal voltage of specimen 131 and the current that goes through the specimen 131 can be measured by sampling circuit 117 in the real time.

Leakage current sensor 137 is composed of permalloy which has wide frequency response domain, and is commercially available in wide frequency ranges, e.g., 1 kHz~100 kHz.

Sampling circuit 117 contains an instrumentation amplifier, programmable band-pass filter and analog-to-digital conversion circuit affording high precision.

Figure 2:
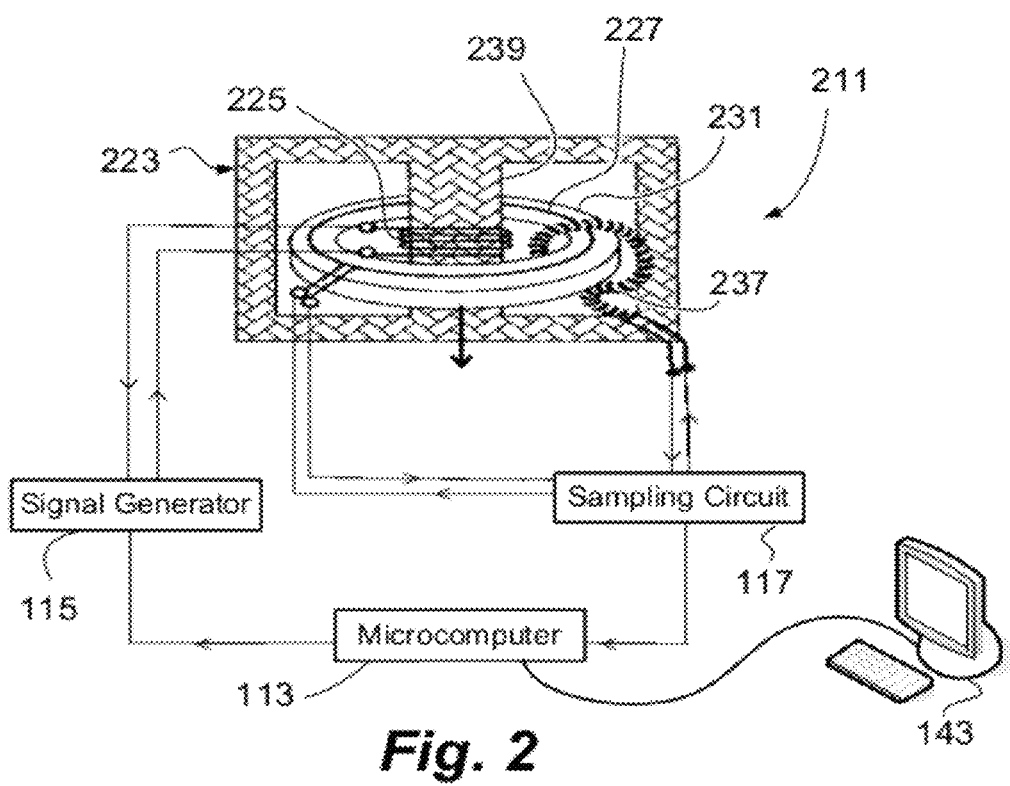
FIG. 2 is a schematic diagram of non-contact impedance (complex resistivity) measurement for a second example configuration.

FIG. 2 is a schematic of a non-contact impedance (complex resistivity) measurement for a second example configuration, in which the transformer is of a double-arm type. Shown are transformer 211, microcomputer 113, signal generator 115, and sampling circuit 117. Transformer 211 includes transformer core 223, primary coil 225 and secondary coil 227. Secondary coil 227 is mounted to or cast inside specimen ring 231, with specimen ring 231 provided as a sample. Leakage current sensor 237 surrounds a portion of secondary coil 227, but is physically separated from secondary coil 227.

In this example configuration, a double arm transformer core 223 is provided, and primary coil 225 is wound around a center pole 239 of transformer core 223. In this system, secondary coil 227 makes a part of specimen ring 231 by mounting secondary coil 227 to specimen ring 231 or casting secondary coil 227 in specimen ring 231. Specimen ring 231 can be annular or rectangular, according to which is easier to mold. Secondary coil 227 is constructed as a single coil surround on an upper surface of the specimen 231, and is able to measure the toroidal voltage of specimen ring 231.

The primary coil surrounds the middle of transformer core 223, while specimen ring 231 and secondary coil 227 pass the windows of the double-arm transformer 211 by extending around center pole 239. The working principle is similar with the configuration of FIG. 1, with microcomputer 113, signal generator 115, sampling circuit 117 and leakage current sensor 237.

In use of the example configurations of FIGS. 1 and 2, an AC voltage is applied to the primary coil and then a toroidal voltage is induced in the specimen ring 131 or 231. By measurement of this toroidal voltage and the induced current flowing in the specimen (specimen ring 131 or 231), the impedance and complex resistivity of the specimen can be calculated to analysis the microstructure development in the specimen as occurs at specimen ring 131 or 231.

In order to get a comprehensive view of the disclosed working mechanism, the cement-based materials are taken as an example. Assuming that the selected frequency domain is 1 kHz~30 kHz, the scanning timing per frequency is 8 seconds; the voltage amplitude applied onto the specimen ring 131 or 231 is 0.5V; the scanning frequency is 1 kHz, 3 kHz, 5 kHz, 10 kHz, 15 kHz and 30 kHz. The sampling interval is 1 minute for each test. The test procedure is as follows:

1. Prepare specimen ring 131 or 231
   a. Weigh the raw materials;
   b. Mix the raw materials for 2 minutes in planetary-type mixer at 45 revolutions per minute followed by 2 minutes at 90 revolutions per minute.
2. Measure impedance or complex resistivity of the specimen ring 131 or 231.
   a. Cast the mixture into the ring-shaped mold right after mix. In the prototype configuration, the mold joints were sealed with vacuum grease to prevent water leakage. The slurry was vibrated to drive the air bubbles out until satisfactory compaction was achieved. Test specimen ring 131 or 231 was covered with the attached lid and sealed with adhesive tape to prevent evaporation of water in the hydrating system during the whole testing. Since the resistivity measurements are conducted at the early hydration stage (normally within 1 day), the cement specimen 131 or 231 could be assumed to be saturated; that is, all the pores are filled by the conductive pore solution.
   b. Start the impedance measurement immediately right after the casting, usually about 15 minutes after the mixing. In the program of microcomputer 113, the parameter of the system can be altered in accordance with the experimental conditions. In the prototype configuration, these parameters are set as follows: The applied amplitude of the sine wave is 0.5V. Sweep frequencies are 1 kHz, 3 kHz, 5 kHz, 10 kHz, 15 kHz and 30 kHz, respectively. The interval at every frequency is about 8 seconds. Thus, the total time is 48 seconds, and then the apparatus has a 1 minute sampling interval. When the system starts up, microcomputer 113 is the core of the system, and sends particular commands to signal generator 115. The designed sine wave with specific amplitude and frequency is generated from signal generator 115, and then applied to the transformer 123 or 223 via a high power amplifier which is part of signal generator 115. As a consequence a toroidal voltage is induced from the cement-based specimen ring 131 or 231 and this voltage is measured by secondary coil 127 or 227 surrounded on an upper surface of the specimen ring 131 or 231. Leak current sensor 137 or 237 is provided surrounding a section of the specimen ring 131 or 231 to measure the current flowing in secondary coil 127 or 227 and specimen ring 131 or 231. Hence, both voltage and current in the specimen ring 131 or 231 are measured by sampling circuit 117. Finally, the impedance data of the specimen ring 131 or 231 is sent back to the microcomputer 113 again and revealed on external computer 143. The operation is continuous.
   c. Keep a relative stable temperature and humidity during the test environment.
   d. Stop the test at any time as needed, and calibrate the resistivity by measuring the height of the specimen ring 131 or 231.
   e. Process impedance data with smoothing for further analysis.
3. Analyze data
   a. Obtain the real, imaginary and phase lag of complex resistivity or impedance curves to identify hydration stages;
   b. Interpret the hydration process and microstructure development.

In the three examples below, Portland cement meeting the requirement of ASTM Type I was used for all specimens. All specimens were tested at room temperature (25° C.).

Cement Paste Example 1

Figure 3A:
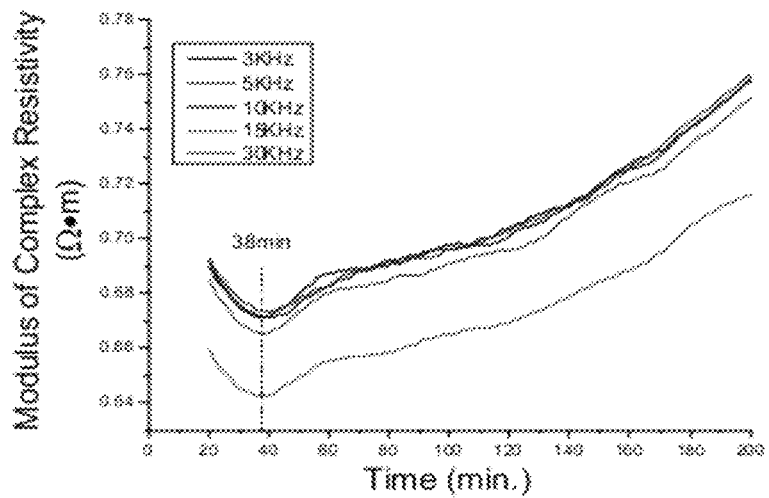
FIGS. 3A-E are graphic depictions which demonstrate the complex resistivity of the Cement Paste Example 1.

FIGS. 3A-D are graphic depictions which demonstrate the complex resistivity of the cement paste Example 1. In Example 1, water/cement (w/c) ratio is 0.4 and applied voltage is 0.6V. The modulus, real part, imaginary part, phase lag of complex resistivity are shown, in which:

FIG. 3A shows the modulus of complex resistivity. The plots for 3, 5 and 10 kHz appear near the top and approximately coincide. The plot for 15 kHz is slightly below the plots for 3, 5 and 10 kHz. The plot for 30 kHz is below the other plots.

Figure 3B:
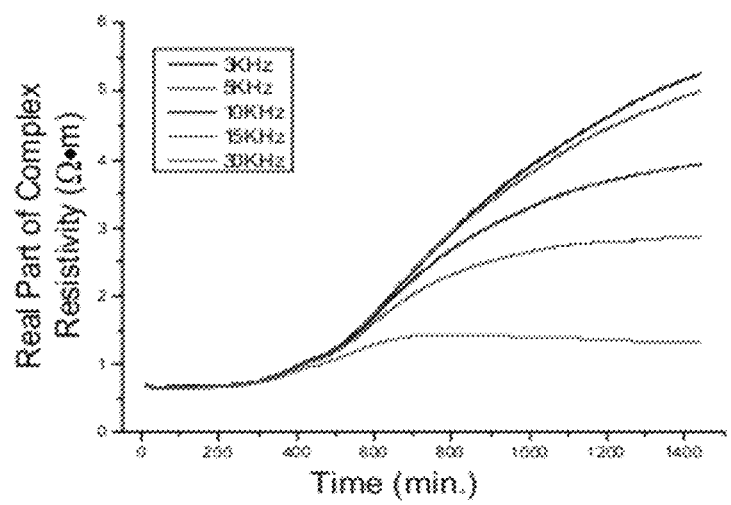

FIG. 3B shows the real part of complex resistivity. The plots are, in order from top to bottom, 3, 5, 10, 15 and 30 kHz.

Figure 3C:
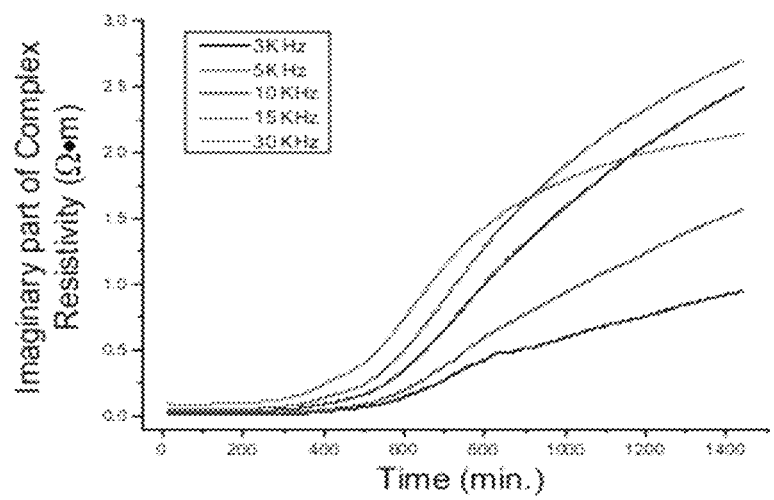

FIG. 3C shows the imaginary part of complex resistivity. In the center of the chart, the plots are, in order from bottom to top p, 3, 5, 10, 15 and 30 kHz. On the right, the plot for 30 kHz can be seen dipping below the plots for 15 and 10 kHz.

Figure 3D:
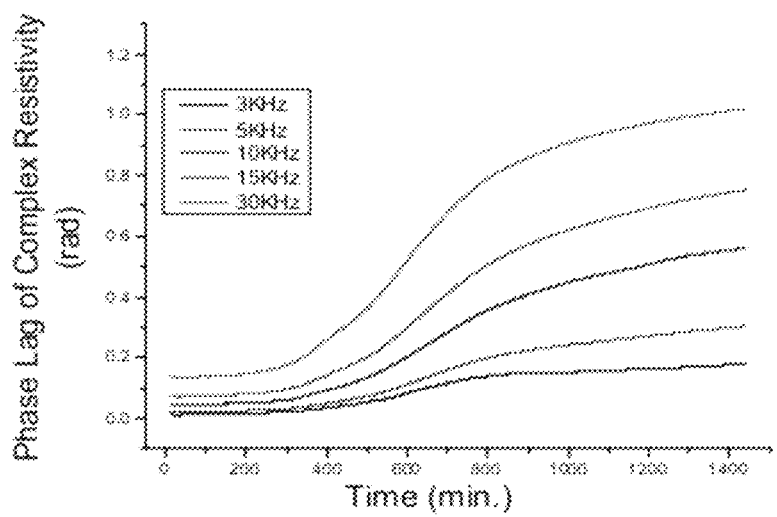

FIG. 3D shows the phase lag of complex resistivity. The plots are, in order from bottom to top, 3, 5, 10, 15 and 30 kHz.

The paste with water/cement (w/c) ratio 0.4 is evaluated, and the applied voltage onto the paste is 0.6V. The test procedure is as follows:

Prepare specimen by weighing the raw materials and mixing the raw materials for 2 minutes in a vertical-axis pan mixer at low rotational speed and for a further 2 minutes at high speed.

Measure the complex resistivity of the specimen.

The measurement is performed with the mixture cast into a ring-shaped mold immediately after mixing. The resistivity measurement started right after casting and the data were automatically recorded by a computer. Sweep frequencies are 3 kHz, 5 kHz, 10 kHz, 15 kHz and 30 kHz, respectively. The interval at every frequency is about 8 seconds. Thus, the total time is 40 seconds, and the apparatus automatically recorded with 1 minute sampling interval. The operation was continuous. Data in one day from casting were processed with smoothing.

The modulus and phase lag of complex resistivity in the testing specimen can be obtained from raw data sets.

$$\rho_c' = |\rho_c| \times \cos \theta$$

and $$\rho_c'' = |\rho_c| \times \sin \theta$$

where $|\rho_c|$ is the modulus of the complex resistivity; $\rho_c'$ is real part of the complex resistivity and $\rho_c''$ is the imaginary part of the complex resistivity; and θ is the phase lag between the real part and imaginary part.

These parameters are employed to analyze the hydration process in real time. The real part and imaginary part of complex resistivity, phase lag between the real part and imaginary part for different frequencies are demonstrated in FIGS. 3B, 3C and 3D.

The real part of complex resistivity is referred to as the resistive property of liquid and solid phase in cement-based materials. It can be seen from FIG. 3B that curves from different frequencies are almost identical before 300 minutes, and then show an obvious difference afterwards. This is due to the different peculation characters of the solid hydration product under different frequencies. Hence, the separation point can be used to identify the hydration stage.

The imaginary part of the complex resistivity, shown in FIG. 3C, is determined mainly by the electrical double layer of pore and pore connectivity. At the beginning, the solution is connected in all the portions of the specimen and the values of imaginary part are almost equal to zero. Therefore, not much difference in imaginary response for different frequencies appears in FIG. 3C. With the hydration product development, more solid contents appear and a microstructure with porosity forms. At that time, the imaginary response increases and shows the different values for different frequencies. All of the imaginary part of the complex resistivity is positive due to the inductive behavior of tortuous pores.

FIG. 3D is the phase lag of complex resistivity development. Here, it is assumed that the phase of the applied voltage is always zero. The entire phase lag is positive, which coincides with FIG. 3C. It is noted that the higher frequency curve reflects a larger value, which corresponds to electromagnetic wave penetration performance in the real part of the complex resistivity.

Figure 3E:
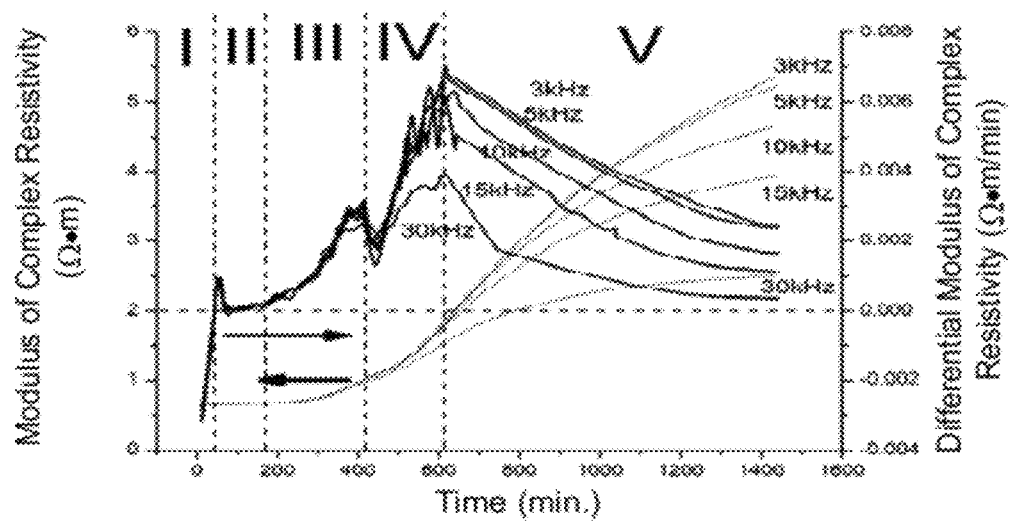

FIG. 3E is a diagram showing a modulus and differential modulus of complex resistivity. The modulus of complex resistivity is given in Ω·m, on the scale on the left. The differential modulus of complex resistivity is given in (Ω·m)/min, on the scale on the right.

From FIG. 3E above, five stages of the hydration can be identified from the characteristic points of complex resistivity and its differential curve: the dissolution stage (I), (0~0.5 h) from the beginning to the minimum modulus point; the competition stage (II), (0.5~3 h) from minimum modulus point to the end of flat zero stage of differential of modulus; the setting stage (III), (3~6.5 h) from the end of flat zero stage to the first peak of differential of modulus curves; the hardening stage (IV), (6.5-10 h) from the first peak to the second peak of differential of modulus curves; and the hardening deceleration stage (V), (>10 h) after the second peak of differential of modulus curves.

The first four stages (I-IV) are the first four stages at the beginning of hydration in cement-based materials.

The dissolution stage (I) occurs from the mixing time to the minimum point time. In this stage, the rate of the modulus curves is less than zero and the dissolution of cement particles is dominant. Ions are rapidly released from the surface of cement grains and dissolved into the solution. At this stage, hydration reactions start to take place. The electrical resistivity decreases due to the increase of ionic concentrations and the mobility of these ions.

The competition stage (II) occurs from the minimum point time to the end of flat zero stage. The rate of the modulus curves is very close to zero, which demonstrates the competition of consuming and releasing ions results in a dynamic balance. In this stage, the ions in the solution are gradually absorbed by the formation of hydrated products. Such initial hydration reactions consume a few ions, which reduces ion concentration. Meanwhile, additional ions continue to release from the surface of unhydrated cement grains and are allowed to dissolve in the mixture.

The setting stage (III) occurs from the end of flat zero stage to the first peak point of the differential curve. The rate of the modulus curves increases sharply. In this stage, the rapid increase of resistivity is related to a significant decrease in the number of ionic species due to the rapid formation of gel product, ettringite and calcium hydroxide, leading to hardening. This stage always coincides with strong heat generation (exothermic reaction) associated with the hydration process.

The hardening stage (IV) occurs from the first peak point time to the second peak of differential of modulus curves. The resistivity development of specimen becomes ion diffusion controlled and presents larger values, because the hydrates have formed an envelope which blocks the way of solution exposure to the unhydrated cement particles. Finally, ion diffusion through the calcium silicate hydrate (C—S—H) layers determines the rate of chemical reaction in the mixture. (C—S—H refers to a cement paste composed of CaO, $SiO_2$ and $H_2O$, but may also include $Fe_2O_3$, $Al_2O_3$ and $SO_3$ and other materials.)

Subsequent to hardening stage IV, the hardening deceleration stage (V) occurs.

Cement Paste Example 2

FIGS. 4 A-C are graphic depictions which demonstrate the complex resistivity of the cement paste Example 2. The water/cement (w/c) ratio is 0.4 and applied voltage is 0.8V. The real part, imaginary part and phase lag of complex resistivity are shown in FIG. 4.

Figure 4A:
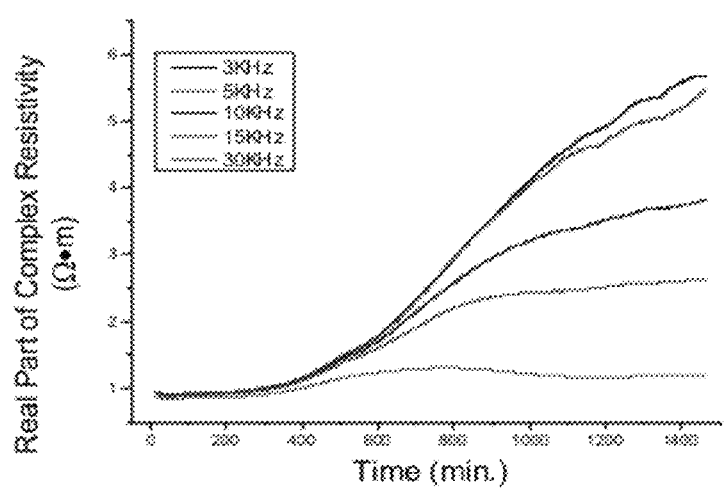
FIG. 4A shows the real part of complex resistivity.

FIG. 4A shows the real part of complex resistivity. The plots are, in order from top to bottom, 3, 5, 10, 15 and 30 kHz.

Figure 4B:
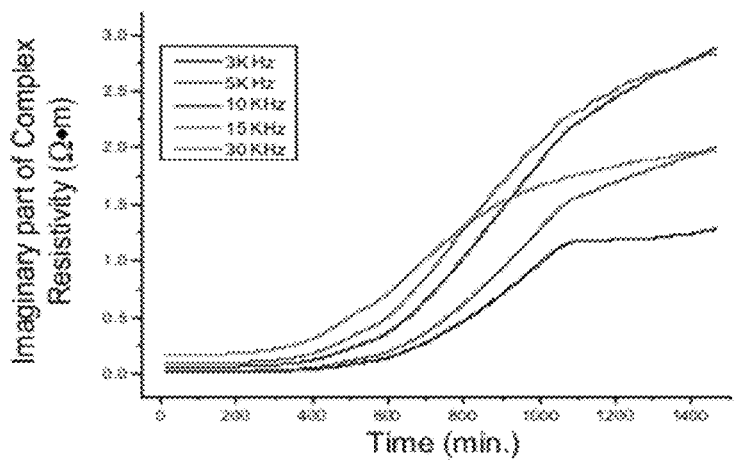
FIG. 4B shows the imaginary part of complex resistivity.

FIG. 4B shows the imaginary part of complex resistivity. In the center of the chart, the plots are, in order from bottom to top, 3, 5, 10, 15 and 30 kHz. On the right, the plot for 30 kHz can be seen dipping below the plots for 15 and 10 kHz.

Figure 4C:
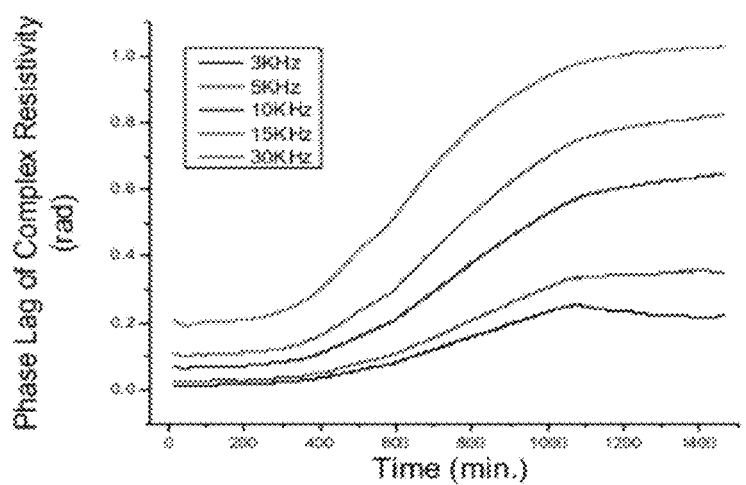
FIG. 4C shows the phase lag of complex resistivity.

FIG. 4C shows the phase lag of complex resistivity. The plots are, in order from bottom to top, 3, 5, 10, 15 and 30 kHz.

The paste with water/cement (w/c) ratio 0.4 is evaluated, and the applied voltage onto the paste is 0.8V. The test procedure is as follows:
Prepare specimen by weighing the raw materials and mixing the raw materials for 2 minutes in a vertical-axis pan mixer at low rotational speed and for a further 2 minutes at high speed.
Measure the complex resistivity of the specimen.

The measurement of complex resistivity is performed by casting the mixture into the ring-shaped mold right after mixing. The resistivity measurement started right after casting and the data were automatically recorded by a computer. Sweep frequencies are 3 kHz, 5 kHz, 10 kHz, 15 kHz and 30 kHz, respectively. The interval at every frequency is about 8 seconds. Thus, the total time is 40 seconds, and the apparatus automatically records with 1 minute sampling interval. The operation was continuous. Data in one day from casting were processed with smoothing.

Cement Paste Example 3

Figure 5:
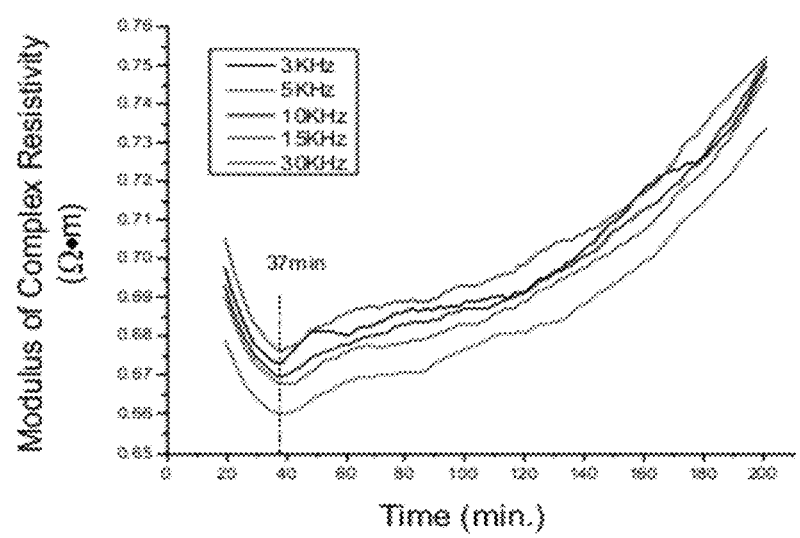
FIG. 5 is a graphic depiction which demonstrates the modulus of complex resistivity in Cement Paste Example 3.

FIG. 5 is a graphic depiction which demonstrates the modulus of complex resistivity in Cement Paste Example 3. The water/cement (w/c) ratio is 0.3 and applied voltage is 0.8V. In the center of the chart, the plots are, in order from bottom to top, 5, 3, 10, 15 and 30 kHz, which places the plot for 3 kHz below that of the plot for 5 kHz. On the right, the plot for 3 kHz can be seen dipping below the plots for 5 and 10 kHz, but is still above the plots for 15 and 30 kHz.

The paste with w/c ratio of 0.3 is evaluated according to the test procedure is as follows:
Prepare specimen by weighing the raw materials and mixing the raw materials for 2 minutes in a vertical-axis pan mixer at low rotational speed and for a further 2 minutes at high speed.
Measure the complex resistivity of the specimen.

As with the above examples, the measurement of complex resistivity is performed by casting the mixture into the ring-shaped mold right after mixing. The resistivity measurement started right after casting and the data were automatically recorded by a computer. As indicated, sweep frequencies are 3 kHz, 5 kHz, 10 kHz, 15 kHz and 30 kHz, respectively. The interval at every frequency is about 8 seconds. Thus, the total time is 40 seconds, and so the apparatus automatically recorded with a 1 minute sampling interval. The operation is continuous. Data in one day from casting were processed with smoothing.

In the examples of FIGS. 3-5, it can be seen that modulus of complex resistivity curves first decrease and then increase after the lowest point is reached. This period corresponds to the dissolving (initial hydrolysis) period in a hydration process. While the real part of complex resistivity is referred to as the resistive property of liquid and solid phase in cement-based materials, which reflects the penetration performance of electromagnetic wave in materials. In addition, the imaginary part of the complex resistivity is determined mainly by the pore heterogeneity and pore connectivity in materials.

CONCLUSION

It will be understood that many additional changes in the details, materials, steps and arrangement of parts, which have been herein described and illustrated to explain the nature of the subject matter, may be made by those skilled in the art within the principle and scope of the invention as expressed in the appended claims. For example, various configurations for transformers and other sympathetic impedance devices can be used, with the intent of obtaining a response as electrical energy is applied to one reactive circuit and sampled from a reactively coupled reactive circuit. Similarly, while the sample has been described as coupled to the secondary coil, it is possible to construct a testing device with the sample coupled to the primary coil.

What is claimed is:

1. An apparatus for measuring impedance and complex resistivity of a sample resulting from a change in a physical or chemical state, the apparatus comprising:
   a signal generator with a frequency synthesizer and a push-pull high power amplifier applying a sine wave signal with amplitude compensation and capable of generating current comprising an AC component;
   a transformer having a primary coil and a secondary coil;
   the primary coil connected to the signal generator, and at least one of the primary and secondary coils having a closed loop and electrically coupled to said sample, whereby an AC voltage applied to the primary coil and inducing a toroidal voltage induces current to flow in the specimen;
   a leakage current sensor;
   a sampling circuit provided as an integral circuit to obtain electrical parameters in a non-contact manner, including the real part and imaginary part of impedance as a measurement of complex resistivity, reflecting permeability, mobility, concentration and distribution of the charge carriers, the sampling circuit comprising a high precision instrumentation amplifier, programmable band-pass filter and digital conversion circuit, wherein the obtaining of electrical parameters to obtain the real part and imaginary part of impedance comprises applying a waveform at a plurality of sweep frequencies for predetermined intervals to induce a toroidal voltage from the sample, with a resultant voltage and current measured by the sampling circuit; and
   a microcomputer controlling the sampling circuit and programmed to accurately modulate the frequency and amplitude of the signal generator and effect sampling at the plurality of sweep frequencies by controlling at least one of the signal generator and the sampling circuit to cause sensing of signals from the signal generator as transmitted through the secondary coil of the transformer at the plurality of sweep frequencies and sensing of the leakage current.

2. The apparatus of claim 1, wherein the coil electrically coupled to said sample comprises said coil mounted to or cast inside a specimen ring.

3. The apparatus of claim 1, wherein the coil electrically coupled to said sample comprises the secondary coil mounted to or cast inside a specimen ring.

4. The apparatus of claim 1, wherein:
the signal generator comprises, as the frequency synthesizer, a direct digital synthesizer.

5. The apparatus of claim 1, wherein:
the transformer comprises a manganese zinc ferrite core; and
the leakage current sensor comprises a permalloy coil.

6. The apparatus of claim 1, wherein the sampling at the plurality of sweep frequencies comprises using the signal generator with the function of frequency sweep and amplitude variation.

7. The apparatus as claimed in any claim of claim 1, further comprising:
using, as said secondary coil, said sample formed as a closed loop of liquid phase materials selected from the group comprising molten glass, molten metal, toxic solution, biological solution and cement-based materials.

8. The apparatus as claimed in any claim of claim 1, further comprising:
using, as said secondary coil, said sample formed as a material subject to a hydration reaction.

9. A method of measuring impedance and complex resistivity of a sample resulting from a change in a physical or chemical state, the method comprising:
electrically coupling said sample to a closed loop in at least one of a primary and a secondary coil in a transformer;
providing a frequency-variable signal to a primary coil of the transformer by use of a push-pull high power amplifier applying a sine wave signal with amplitude compensation and capable of generating a current comprising an AC component, and varying the frequency thereof, whereby an AC voltage applied to the primary coil and inducing a toroidal voltage induces current to flow in the specimen;
measuring voltage across the secondary coil
measuring leakage current from the coil electrically coupled to said sample;
using a sampling circuit, provided as an integral circuit to obtain electrical parameters in a non-contact manner, including the real part and imaginary part of impedance as a measurement of complex resistivity, reflecting permeability, mobility, concentration and distribution of the charge carriers, the sampling circuit comprising high precision instrumentation amplifier, programmable band-pass filter and digital conversion circuit, to measure the voltage across the secondary coil and the leakage current as a function of the frequency-variable signal by using a microcomputer controlling the sampling circuit and programmed to accurately modulate the frequency and amplitude, and effecting sampling at a plurality of sweep frequencies at the secondary coil and of the measured leakage current by controlling at least one of the frequency-variable signal and the sampling circuit to cause sensing of the variable frequency signal as transmitted through the secondary coil of the transformer at the plurality of sweep frequencies, wherein the obtaining of electrical parameters to obtain the real part and imaginary part of impedance comprises applying a waveform at the plurality of sweep frequencies for predetermined intervals to induce a toroidal voltage from the sample, with a resultant voltage and current measured by the sampling circuit.

10. The method of claim 9, wherein the measuring of voltage and leakage current obtains measured parameters comprising electrochemical and dielectric properties of the sample.

11. The method of claim 10, wherein the measuring of voltage and leakage current obtains measured parameters of a pore structure in the sample.

12. The method of claim 9, wherein the measuring of voltage and leakage current identifies hydration degree, maturity and strength development for cement-based materials.

13. A process for measuring parameters of a material under test resulting from a change in physical or chemical state, the method comprising:
preparing a sample of the material under test in electromagnetic communication with at least one of a primary coil and a secondary coil of a transformer;
applying a variable frequency signal from a signal generator with a frequency synthesizer and a push-pull high power amplifier applying a sine wave signal with amplitude compensation and capable of generating current comprising an AC component to a primary coil of the transformer;
sensing a voltage signal across the secondary coil of the transformer, whereby an AC voltage applied to the primary coil and inducing a toroidal voltage induces current to flow in the specimen;
sensing leakage current around the sample;
using a sampling circuit, provided as an integral circuit to obtain electrical parameters in a non-contact manner, including the real part and imaginary part of impedance as a measurement of complex resistivity, reflecting permeability, mobility, concentration and distribution of the charge carriers, the sampling circuit comprising a high precision instrumentation amplifier, programmable band-pass filter and digital conversion circuit, to measure the voltage across the secondary coil and the leakage current as a function of the frequency-variable signal, controlling the sampling circuit and accurately modulating the frequency and amplitude of the signal generator and effect sampling at a plurality of sweep frequencies by controlling at least one of the signal generator and the sampling circuit to cause sensing of signals from the signal generator as transmitted through the secondary coil of the transformer at the plurality of sweep frequencies and sensing of the leakage current, wherein the obtaining of electrical parameters to obtain the real part and imaginary part of impedance comprises applying a waveform at the plurality of sweep frequencies for predetermined intervals to induce a toroidal voltage from the sample, with a resultant voltage and current measured by the sampling circuit.

14. The process of claim 13, further comprising:
wherein said controlling the sampling circuit comprises controlling at least one of the frequency-variable signal and the sampling circuit to cause sensing of the variable frequency signal as transmitted through the secondary coil of the transformer at the plurality of sweep frequencies.

15. The method of claim 13, wherein the measured parameters comprise electrochemical and dielectric properties of the sample.

16. The method of claim 15, wherein the measured parameters comprise a pore structure in the sample.

17. The method of claim 13, wherein the measured parameters identify hydration degree, maturity and strength development for cement-based materials.

18. An apparatus for measuring impedance and complex resistivity of a sample resulting from a change in a physical or chemical state the apparatus comprising:
sympathetic impedance means, comprising signal generating means comprising a frequency synthesizer and a push-pull high power amplifier applying a sine wave signal with amplitude compensation and capable of generating a current, and having at least one of a primary reactive circuit and a secondary reactive circuit electrically coupled to the sample, whereby an AC voltage applied to the primary reactive circuit and inducing a toroidal voltage induces current to flow in the sample;
means for providing a frequency-variable signal to a primary reactive circuit of the sympathetic impedance means, and varying the frequency of the signal;
means for measuring voltage across the secondary reactive circuit;
means for measuring leakage current from the reactive circuit electrically coupled to the sample;
means for sampling the voltage across the secondary reactive circuit and the leakage current as a function of the frequency-variable signal at a plurality of sweep frequencies provided to the sympathetic impedance means by controlling at least one of the frequency-variable signal and a sampling circuit to cause sensing of the frequency-variable signal as transmitted through the secondary reactive circuit at the plurality of sweep frequencies, the means for sampling provided integrally to obtain electrical parameters in a non-contact manner, including the real part and imaginary part of impedance as a measurement of complex resistivity, reflecting permeability, mobility, concentration and distribution of the charge carriers, the sampling circuit comprising a high precision instrumentation amplifier, programmable band-pass filter and digital conversion circuit, wherein the obtaining of electrical parameters to obtain the real part and imaginary part of impedance comprises applying a waveform at a plurality of sweep frequencies for predetermined intervals to induce a toroidal voltage from the sample, with a resultant voltage and current measured by the sampling circuit; and
processing means controlling the means for sampling and programmed to accurately modulate the frequency and amplitude of the signal generating means and effect the sampling at plurality of sweep frequencies by controlling at least one of the signal generating means and the means for sampling to cause sensing of signals from the signal generating means as transmitted across the secondary reactive circuit at the plurality of sweep frequencies and sensing of the leakage current.

19. The apparatus of claim 18, wherein the measuring of voltage and leakage current obtains measured parameters comprising comprise electrochemical and dielectric properties of the sample.

20. The apparatus of claim 19, wherein the measuring of voltage and leakage current obtains measured parameters of a pore structure in the sample.

21. The apparatus of claim 18, wherein the measuring of voltage and leakage current identifies hydration degree, maturity and strength development for cement-based materials.

* * * * *